(12) United States Patent
Hyodo et al.

(10) Patent No.: US 10,413,164 B2
(45) Date of Patent: Sep. 17, 2019

(54) MANIPULATOR AND MANIPULATOR SYSTEM

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/682,824

(22) Filed: Aug. 22, 2017

(65) Prior Publication Data

US 2017/0347859 A1  Dec. 7, 2017

Related U.S. Application Data

(63) Continuation of application No. PCT/JP2016/053546, filed on Feb. 5, 2016.

(30) Foreign Application Priority Data

Feb. 26, 2015  (JP) .................................. 2015-036034

(51) Int. Cl.
*A61B 1/00* (2006.01)
*A61B 1/005* (2006.01)
(Continued)

(52) U.S. Cl.
CPC ........ *A61B 1/0057* (2013.01); *A61B 1/00009* (2013.01); *A61B 1/0055* (2013.01);
(Continued)

(58) Field of Classification Search
CPC ... A61B 1/0057; A61B 1/00087; A61B 90/06; A61B 17/00234; A61B 1/00009;
(Continued)

(56) References Cited

U.S. PATENT DOCUMENTS 3,335,620 A * 8/1967 Vertut ...................... B25J 3/00
74/108
4,865,376 A * 9/1989 Leaver .................. B25J 9/1045
901/21
(Continued)

FOREIGN PATENT DOCUMENTS

EP  2415418 A1  2/2012
JP  H11-320464 A  11/1999
(Continued)

OTHER PUBLICATIONS

English Translation of PCT/ISA/237 dated Mar. 29, 2016 in PCT/JP2016/053546 (Year: 2016).*
(Continued)

*Primary Examiner* — Victor L MacArthur
(74) *Attorney, Agent, or Firm* — Scully, Scott, Murphy & Presser, P.C.

(57) ABSTRACT

A manipulator includes:
an operating unit, and
a bending assembly that is bent by operation of the operating unit,
wherein:
the bending assembly includes:
a first link member having a first arc portion,
a second link member having a second arc portion,
an intermediate link member that includes a first intermediate arc portion and a second intermediate arc portion in opposition to the first intermediate arc portion, and is mounted between the first link member and the second link member.

3 Claims, 17 Drawing Sheets

(51) Int. Cl.
*B25J 17/00* (2006.01)
*B25J 18/06* (2006.01)
*A61B 90/00* (2016.01)
*A61B 34/00* (2016.01)
*A61B 17/00* (2006.01)
*B25J 13/04* (2006.01)
*A61B 17/28* (2006.01)
*A61B 1/008* (2006.01)
*A61B 34/30* (2016.01)

(52) U.S. Cl.
CPC .... *A61B 1/00133* (2013.01); *A61B 17/00234* (2013.01); *A61B 34/71* (2016.02); *A61B 90/00* (2016.02); *A61B 90/06* (2016.02); *B25J 13/04* (2013.01); *B25J 17/00* (2013.01); *B25J 18/06* (2013.01); *A61B 1/008* (2013.01); *A61B 1/00087* (2013.01); *A61B 17/28* (2013.01); *A61B 2017/003* (2013.01); *A61B 2017/00314* (2013.01); *A61B 2017/00323* (2013.01); *A61B 2034/305* (2016.02); *A61B 2034/715* (2016.02); *A61B 2090/064* (2016.02)

(58) Field of Classification Search
CPC ..... A61B 34/71; A61B 1/00133; A61B 17/28; A61B 90/00; A61B 2090/064; A61B 2017/00314; B25J 13/04; B25J 18/06; B25J 17/00
See application file for complete search history.

(56) References Cited

U.S. PATENT DOCUMENTS

| | | | | |
|---|---|---|---|---|
| 5,062,673 A | * | 11/1991 | Mimura | ............... B25J 15/0009 901/34 |
| 5,570,920 A | * | 11/1996 | Crisman | .................. B25J 9/104 901/36 |
| 5,710,870 A | * | 1/1998 | Ohm | ......................... B25J 3/04 901/27 |
| 5,784,542 A | | 7/1998 | Ohm et al. | |
| 5,810,716 A | | 9/1998 | Mukherjee et al. | |
| 5,828,813 A | * | 10/1998 | Ohm | ......................... B25J 3/04 901/28 |
| 6,668,678 B1 | | 12/2003 | Baba et al. | |
| 8,342,586 B2 | * | 1/2013 | Sim | ........................... B25J 5/00 901/13 |
| 2004/0036438 A1 | | 2/2004 | Yamagishi | |
| 2004/0199147 A1 | | 10/2004 | Nishizawa et al. | |
| 2013/0213170 A1 | | 8/2013 | Kim et al. | |
| 2014/0331798 A1 | | 11/2014 | Shim et al. | |

FOREIGN PATENT DOCUMENTS

| | | |
|---|---|---|
| JP | 2003-001580 A | 1/2003 |
| JP | 2004-122286 A | 4/2004 |
| JP | 2004-306224 A | 11/2004 |
| JP | 2014-217943 A | 11/2014 |
| WO | 2012/049623 A1 | 4/2012 |

OTHER PUBLICATIONS

International Search Report dated Mar. 29, 2016 issued in PCT/JP2016/053546.

Extended Supplementary European Search Report dated Sep. 4, 2018 in European Patent Application No. 16 75 5179.5.

* cited by examiner

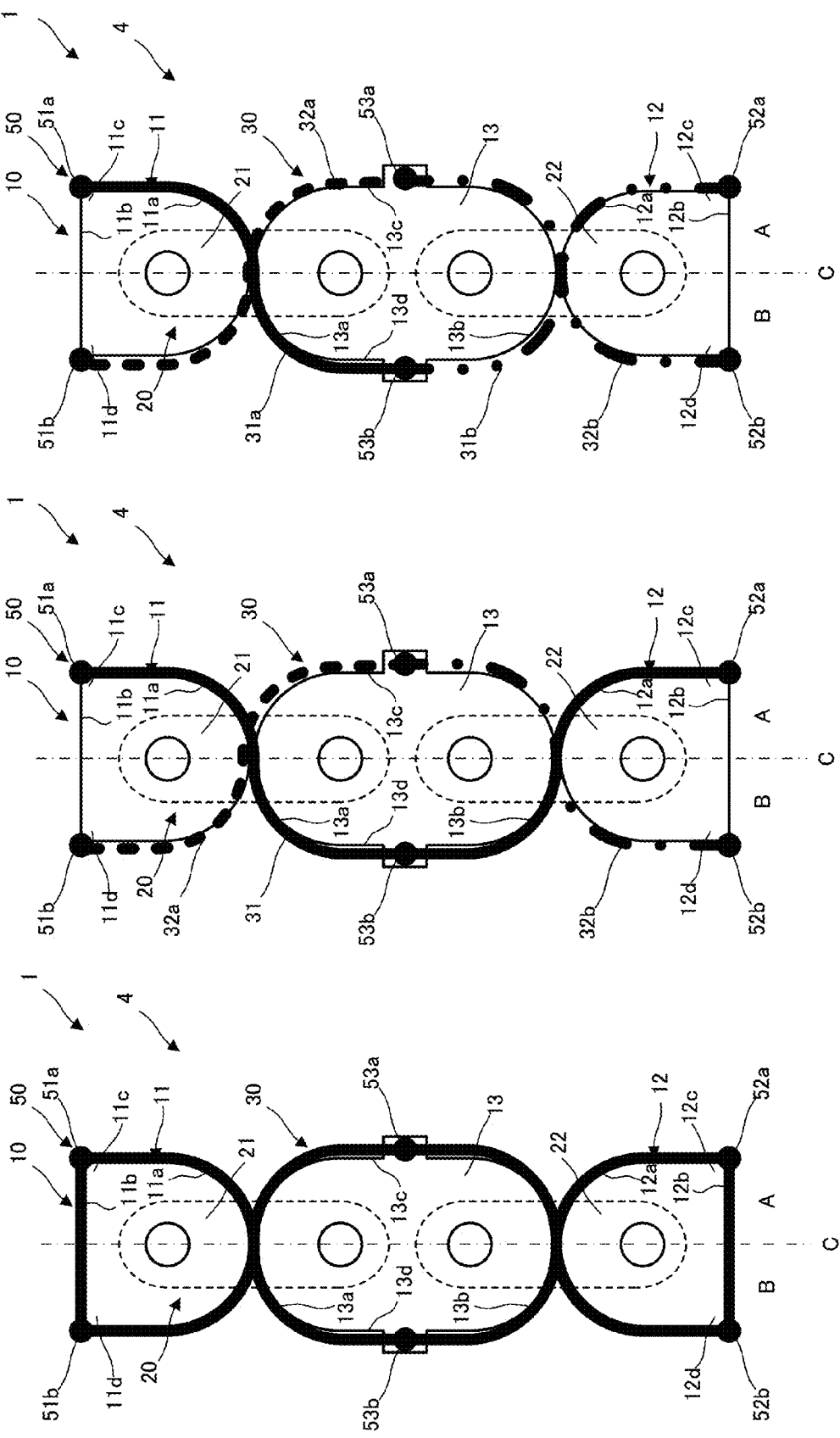

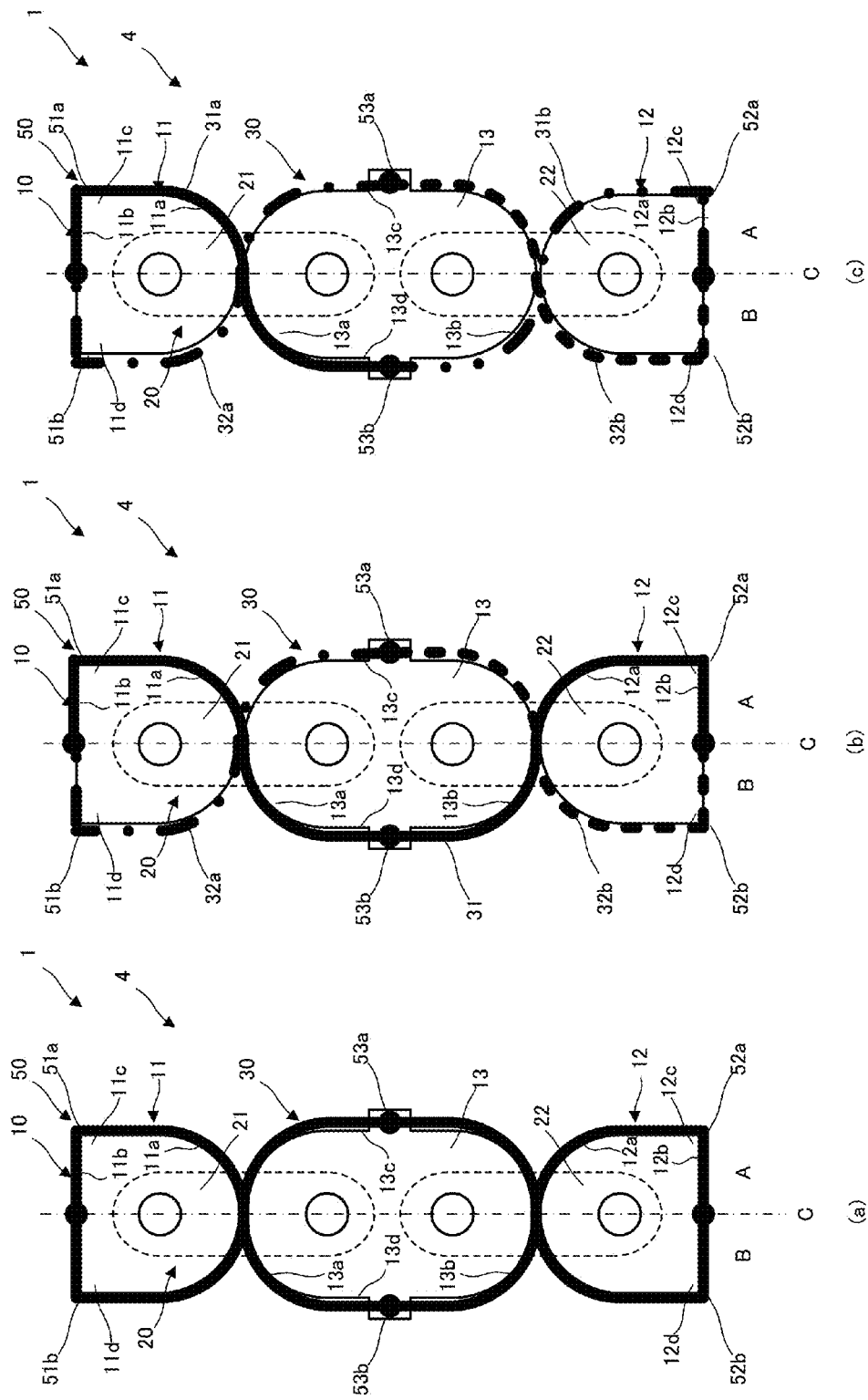

MANIPULATOR AND MANIPULATOR SYSTEM

CROSS-REFERENCE TO RELATED APPLICATIONS

This application is a continuation claiming priority on the basis of Japan Patent Application No. 2015-036034 applied in Japan on Feb. 26, 2015 and based on PCT/JP2016/053546 filed on Feb. 5, 2016. The contents of both the PCT application and the Japan Application are incorporated herein by reference.

BACKGROUND OF THE INVENTION AND RELATED ART STATEMENT

The present invention relates to a manipulator and a manipulator system including a joint assembly that is bent for various treatments and so on.

Typically there has been a manipulator used including a treatment tool inserted into the body cavity of a patient, wherein the distal end of the treatment tool is pulled and bent as by a wire for treatments. Often in surgical operations, a plurality of treatment tools such as an endoscope for viewing, a forceps for holding tissues and an electrical knife for dissecting tissues are inserted into the body cavity.

A pertinent prior publication (U.S. Pat. No. 5,784,542) discloses a manipulator structure wherein a guide wire is located in such a way as to intersect itself between the base members and the guide wire is fixed at its end so that the base members move in rolling contact with each other while movements of joints between the base members are constrained by the guide wire. With such structure, the base members are unlikely to slip because the guide wire will receive a load resulting from sliding movement of the base members when the joints are bent.

SUMMARY OF INVENTION

According to one embodiment, a manipulator includes:
an operating unit, and
a bending assembly that is bent by operation of the operating unit, wherein:
the bending assembly includes:
a first link member having a first arc portion,
a second link member having a second arc portion,
an intermediate link member that includes a first intermediate arc portion and a second intermediate arc portion in opposition to the first intermediate arc portion, and is mounted between the first link member and the second link member,
a first coupling member that couples the first link member to the intermediate link member,
a second coupling member that couples the second link member to the intermediate link member, and
a regulating member that intersects itself between, and is wound around, the first arc portion of the first link member and the first intermediate arc portion of the intermediate link member and intersects itself between, and is wound around, the second arc portion of the second link member and the second intermediate arc portion of the intermediate link member such that the first arc portion and the first intermediate arc portion as well as the second arc portion and the second intermediate arc portion roll.

BRIEF DESCRIPTION OF DRAWINGS

FIGS. 5A, 5B and 5C are illustrative of another example of how to wind the regulating member according to the first embodiment.
FIGS. 7A, 7B and 7C are illustrative of another example of how to wind the regulating member according the second embodiment.

DESCRIPTION OF EMBODIMENTS

The present invention will now be explained with reference to some embodiments.

Figure 1:
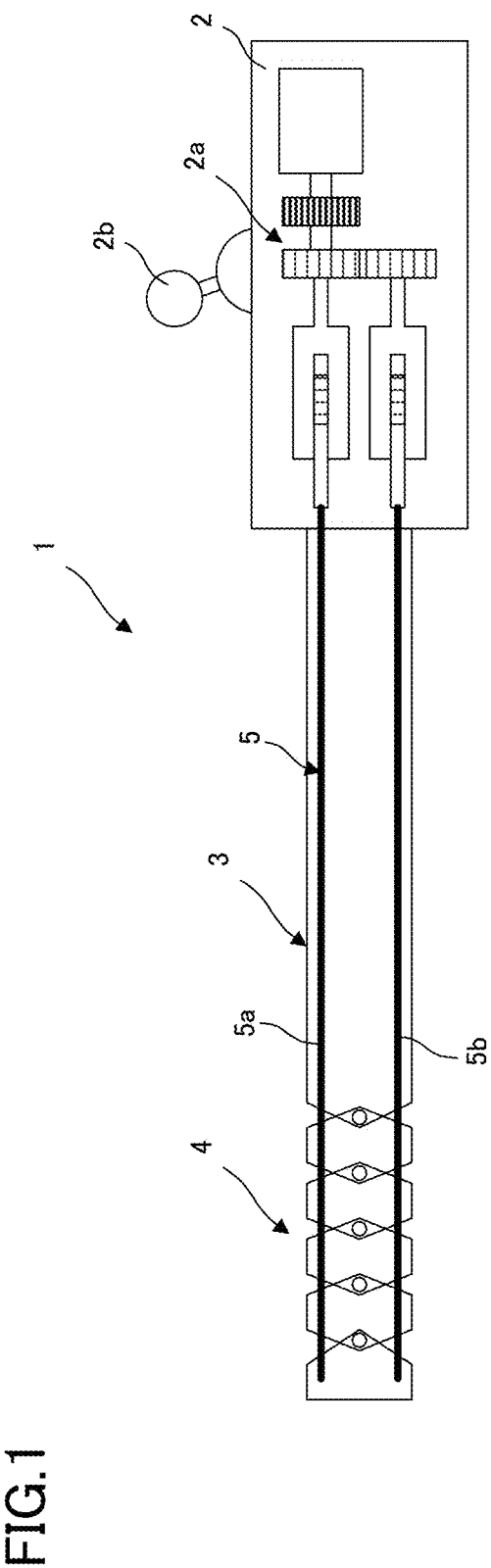
FIG. 1 is illustrative of the manipulator described herein.

FIG. 1 shows a manipulator 1 described herein.

The manipulator 1 described herein includes a main unit 2, an elongated component 3 that extends from the main unit 2, a bending assembly 4 that is connected to the elongated component 3, and a power transmission component 5 typically made up of a wire for transmission of power that actuates the bending assembly 4.

The main unit 2 includes a driving unit 2a including a motor for producing power transmitted to the power transmission component 5, a gear and the like, and a driving unit-operating component 2b for putting the driving unit 2a into operation. The main unit 2 is defined by a case-like portion for housing the driving unit 2a. In the first embodiment, the elongated component 3 adapted to house the power transmission component 5 extends from the main unit 2. The elongated component 3 is provided at its distal end with the bending assembly 4 that is capable of being flexed or bent relative to the elongated component 3. The power transmission component 5 includes a first power transmission member 5a and a second power transmission member 5b each of which is formed of a wire or the like and mounted on one end side to the bending assembly 4, and passes through the elongated component 3, and is mounted on the other end side to the driving unit 2a.

With the manipulator 1 of such structure in normal operation, the driving unit-operating component 2b is put into operation to bend the bending assembly 4. As the driving unit-operating component 2b is put into operation, it causes the driving unit 2a to be driven. The first 5a or the second power transmission member 5b is pulled by power generated by the driving unit 2a. The thus pulled power transmission component 5 moves through the elongated component 3 to pull one side of the bending assembly 4 so that the bending assembly 4 is bent.

Figure 2:
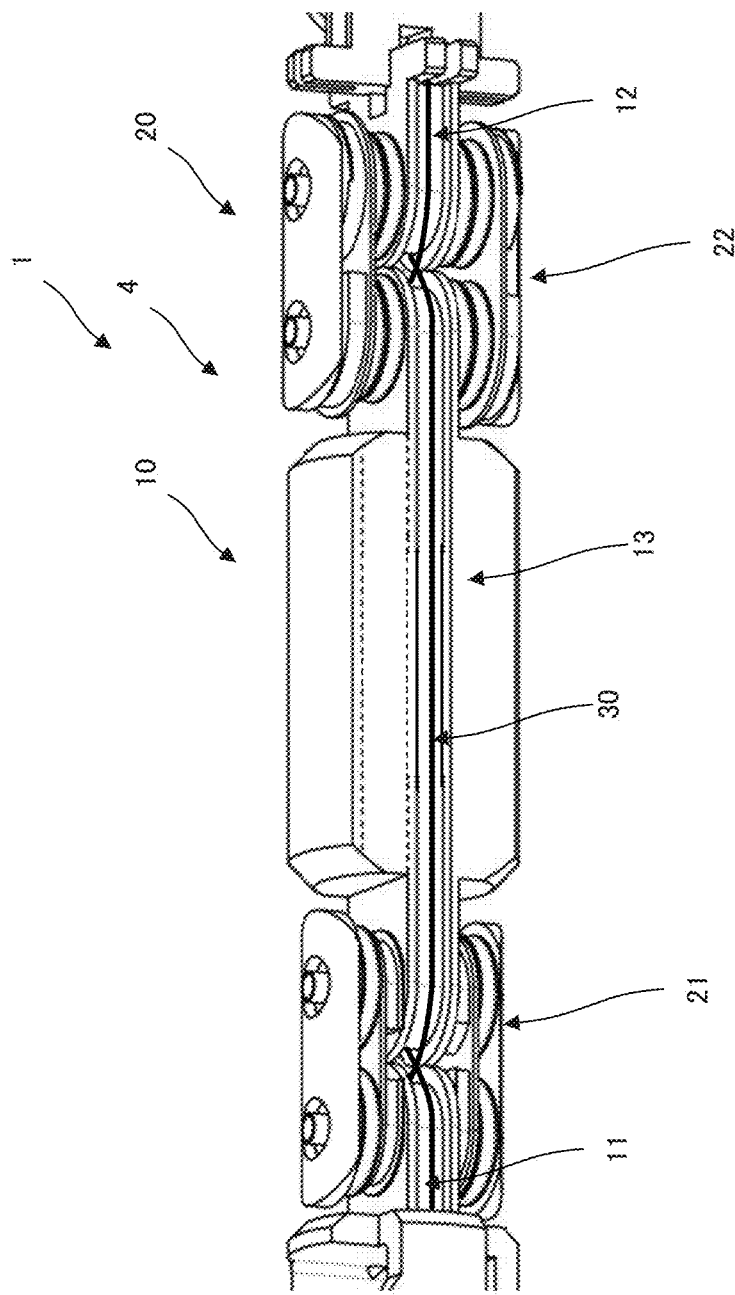
FIG. 2 shows a portion of the bending assembly in the manipulator described herein.

FIG. 2 shows a portion of the bending assembly 4 in the manipulator 1 according to the first embodiment.

In the manipulator 1 described here, the bending assembly 4 includes at least one joint component 10. The joint component 10 includes a first link member 11, a second link member 12, an intermediate link member 13 mounted between the first link member 11 and the second link member 12, a first coupling member 21 that couples the first link member 11 to the intermediate link member 13, a second coupling member 22 that couples the second link member 12 to the intermediate link member 13, and a regulating member 30 including a linear member or the like that is wound around the first link member 11, the second link member 12 and the intermediate link member 13. Note here that the bending assembly 4 may include a plurality of joint components 10.

Figure 3:
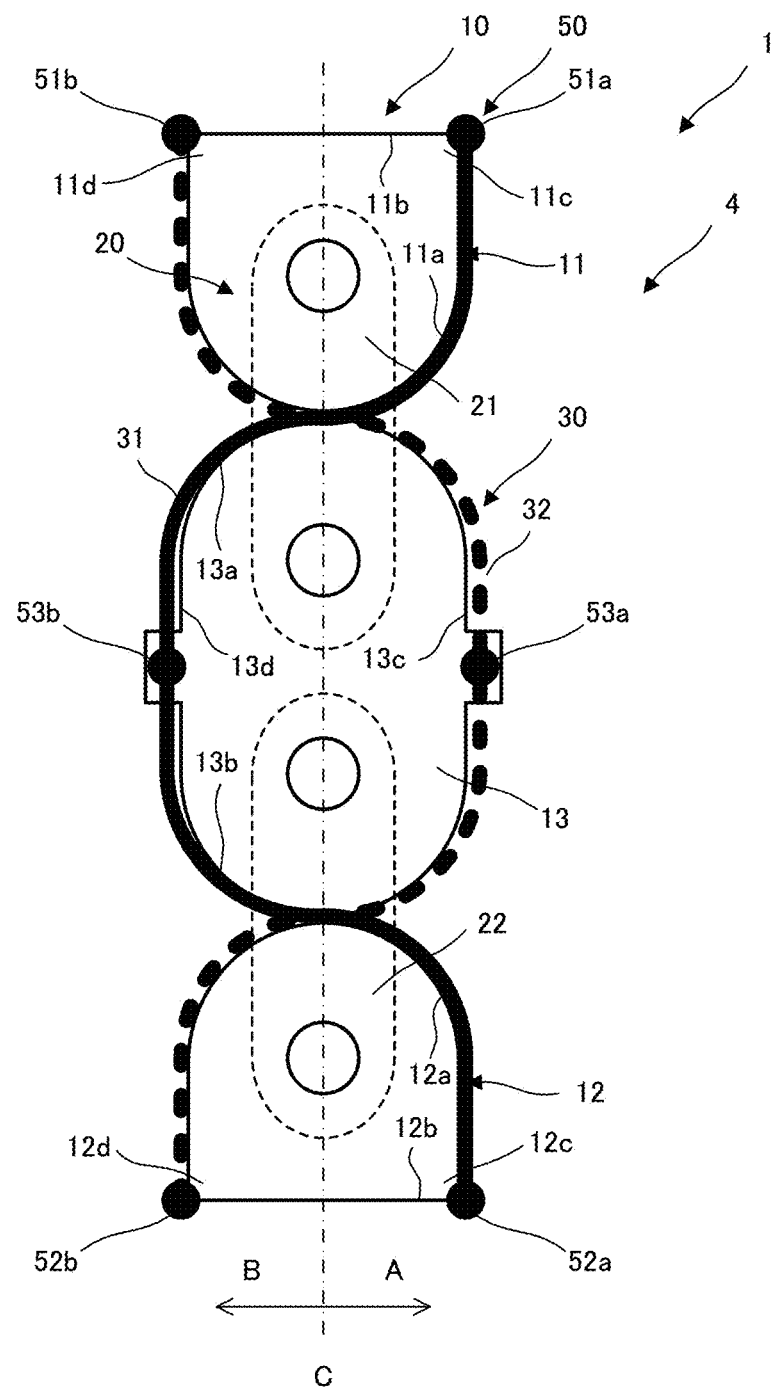
FIG. 3 shows a portion of the bending assembly in the manipulator according to the first embodiment.

FIG. 3 shows a portion of the bending assembly 4 in the manipulator 1 according to the first embodiment.

In the bending assembly 4 in the manipulator 1 according to the first embodiment, two regulating members 30 for each joint component 10 are fixed to the first 11, the second 12 and the intermediate link member 13 at six fixing sites 50.

The first link member 11 includes a first arc portion 11a, a first end surface 11b, a first corner portion 11c on one side and a first corner portion 11d on the other side, and the second link member 12 includes a second arc portion 12a, a second end surface 12b, a second corner portion 12c on one side and a second corner portion 12d on the other side. The intermediate link member 13 includes a first intermediate arc portion 13a in contact with the first arc portion 11a, a second intermediate arc portion 13b in contact with the second arc portion 12a, an intermediate surface 13c on one side and an intermediate surface 13d on the other side.

The coupling member 20 includes a first coupling member 21 that couples the first link member 11 to the intermediate link member 13, and a second coupling member 22 that couples the second link member 12 to the intermediate link member 13. Note here that A and B are indicative of one side and the other side, respectively, with respect to line C connecting the centers of rotation of the coupling members 20.

The fixing site 50 includes a first link one-side fixing portion 51a formed on one side A of the first link member 11, a first link other-side fixing portion 51b formed on the other side B of the first link member 11, a second link one-side fixing portion 52a formed on one side A of the second link member 12, a second link other-side fixing portion 52b formed on the other side B of the second link member 12, an intermediate link one-side fixing portion 53a formed on one side A of the intermediate link member 13, and an intermediate link other-side fixing portion 53b formed on the other side B of the intermediate link member 13. Note here that the fixing site 50 may be provided by caulking, brazing or the like.

Referring typically to the fixing site 50 for the first link member 11, the first link one-side fixing portion 51a is defined by the one-side first corner portion 11c and the first link other-side fixing portion 51b is defined by the other-side first corner portion 11d. In the fixing site 50 for the second link member 12, likewise, the second link one-side fixing portion 52a is defined by the one-side second corner portion 12c and the second link other-side fixing portion 52b is defined by the other-side second corner portion 12d. In the fixing site 50 for the intermediate link member 13, the intermediate link one-side fixing portion 53a is defined by the one-side intermediate surface 13c and the intermediate link other-side fixing portion 53b is defined by the other-side intermediate surface 13d.

In the example of FIG. 3, two regulating members 30 are used; in other words, there are a first regulating member 31 and a second regulating member 32 provided, each formed of a linear member or the like.

The first regulating member 31 is fixed at one end to the first link one-side fixing portion 51a on one side A of the first link member 11, and wound around at least a part on one side A of the first arc portion 11a. Then, the first regulating member 31 is wound around at least a part on the other side B of the first intermediate arc portion 13a of the intermediate link member 13, and wound around at least a part on the other side B of the second intermediate arc portion 13b. Then, the first regulating member 31 is wound around at least a part on one side A of the second arc portion 12a of the second link member 12, and fixed to the second link one-side fixing portion 52a on one side A. Further, the first regulating member 31 is fixed to the intermediate link other-side fixing portion 53b formed on the other side B of the intermediate link member 13.

The second regulating member 32 is fixed at one end to the first link other-side fixing portion 51b on the other side B of the first link member 11, and wound around at least a part on the other side B of the first arc portion 11a. Then, the second regulating member 32 is wound around at least a part on one side A of the first intermediate arc portion 13a of the intermediate link member 13, and wound around at least a part on one side A of the second intermediate arc portion 13b. Then, the second regulating member 32 is wound around at least a part on the other side B of the second arc portion 12a of the second link member 12, and fixed to the second link other-side fixing portion 52b on the other side B. Further, the second regulating member 32 is fixed to the intermediate link one-side fixing portion 53a formed on the surface on one side A of the intermediate link member 13.

Figure 4:
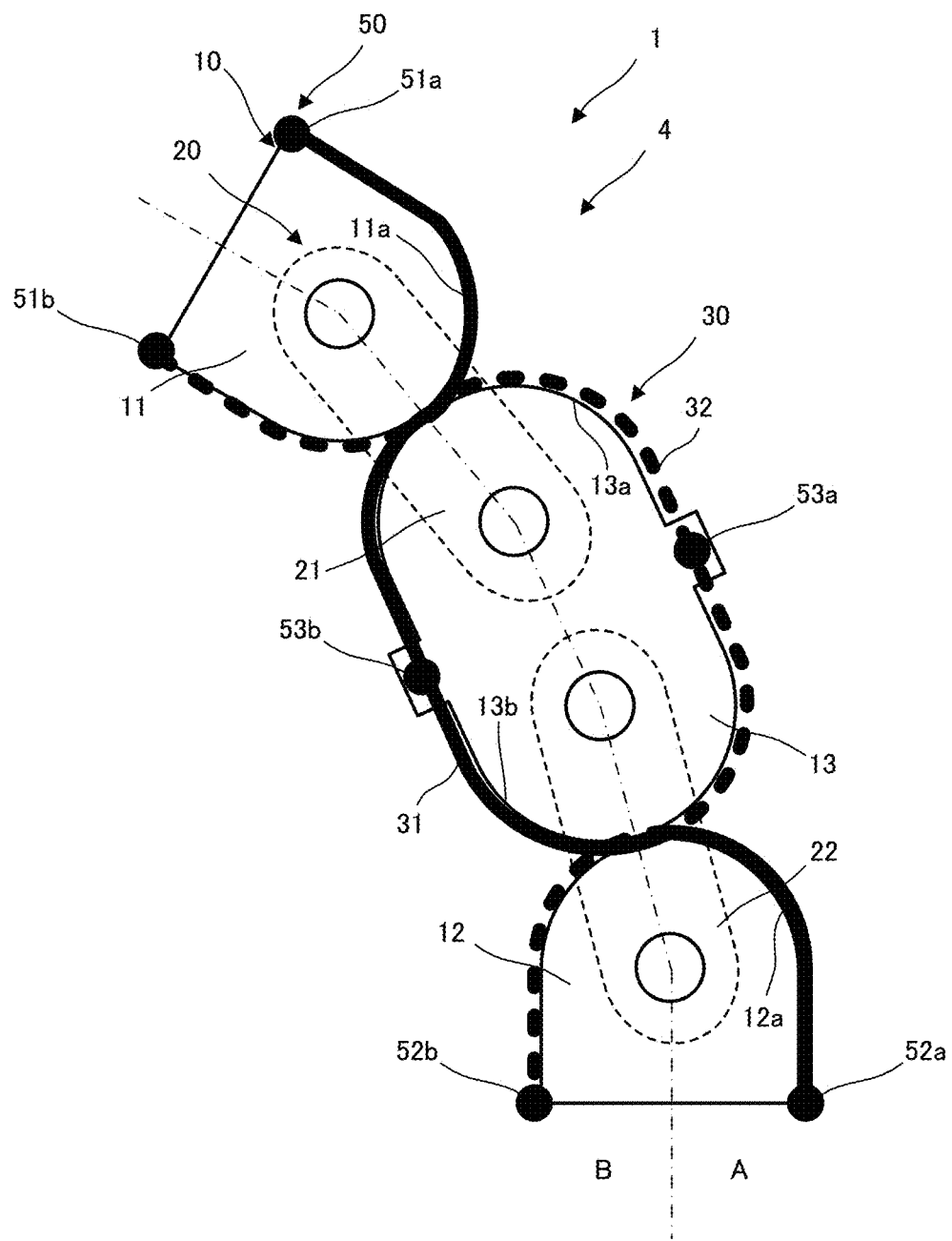
FIG. 4 shows an example of actuation of the bending assembly in the manipulator according to the first embodiment.

FIG. 4 is illustrative of an example of actuation of the bending assembly 4 in the manipulator 1 according to the first embodiment.

More specifically, FIG. 4 shows that the power from the driving unit 2a of FIG. 1 is being transmitted to the power transmission component 5 to bend the distal end side of the bending assembly 4 toward the other side B. The first 31 and the second regulating member 32 are located in such a way as to intersect each other between the first link member 11, the second link member 12 and the intermediate link member 13, and fixed at the fixing sites 50. For this reason, the first regulating member 31 and the second regulating member 32 have a structure of rolling without sliding while constraining movement of the joints between the first 11, the second 12 and the intermediate link member 13.

The bending assembly 4 in the manipulator 1 according to the first embodiment is thus easy to assemble because of a reduced parts count and a simplified structure.

While two regulating members 30 are used in the example of FIG. 4, it is understood that one to four members may be used.

FIGS. 5A, 5B and 5C are illustrative of another example of how to wind the regulating member 30 according to the first embodiment.

FIG. 5A is illustrative of an example of using one regulating member 30, FIG. 5B an example of using three regulating members 30, and FIG. 5C an example of using four regulating members 30.

In the example of FIG. 5A, the regulating member 30 is turned or wound, and fixed at one end and the other end to any of six fixing sites 50. In the example of FIG. 5B, the second regulating member 32 of FIG. 3 is divided into two: a portion 32a that connects the first 11 to the intermediate link member 13 and a portion 32b that connects the second 12 to the intermediate link member 13, providing three regulating members 30. In the example of FIG. 5C, the first regulating member 31 of FIG. 5B is divided into two: a portion 31a that connects the first 11 to the intermediate link member 13 and a portion 31b that connects the second 12 to the intermediate link member 13, providing four regulating members 30.

Figure 6A:
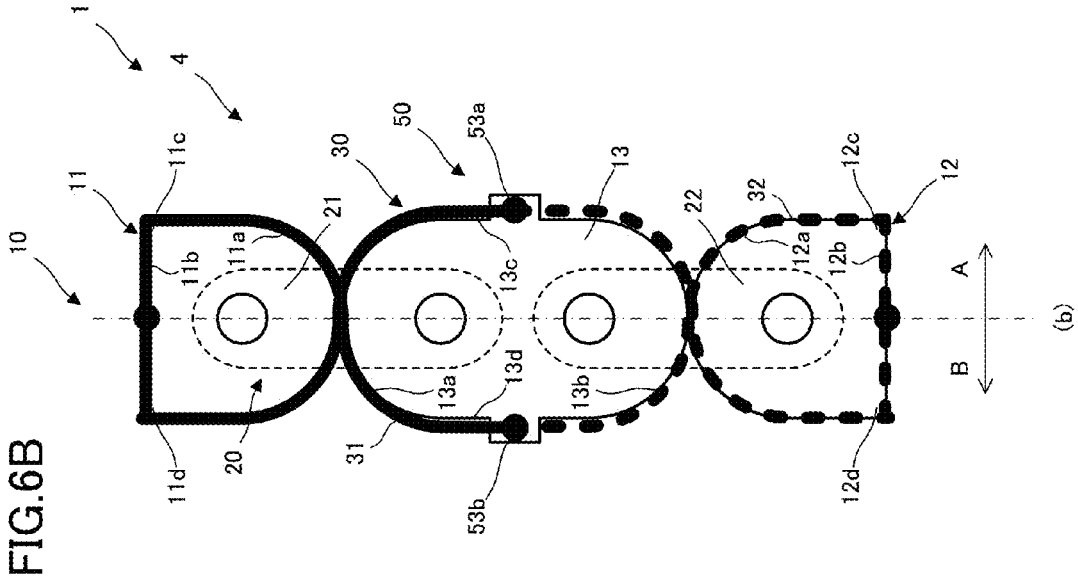
FIGS. 6A and 6B show one example of a portion of the bending assembly in the manipulator according to the second embodiment.
Figure 6B:
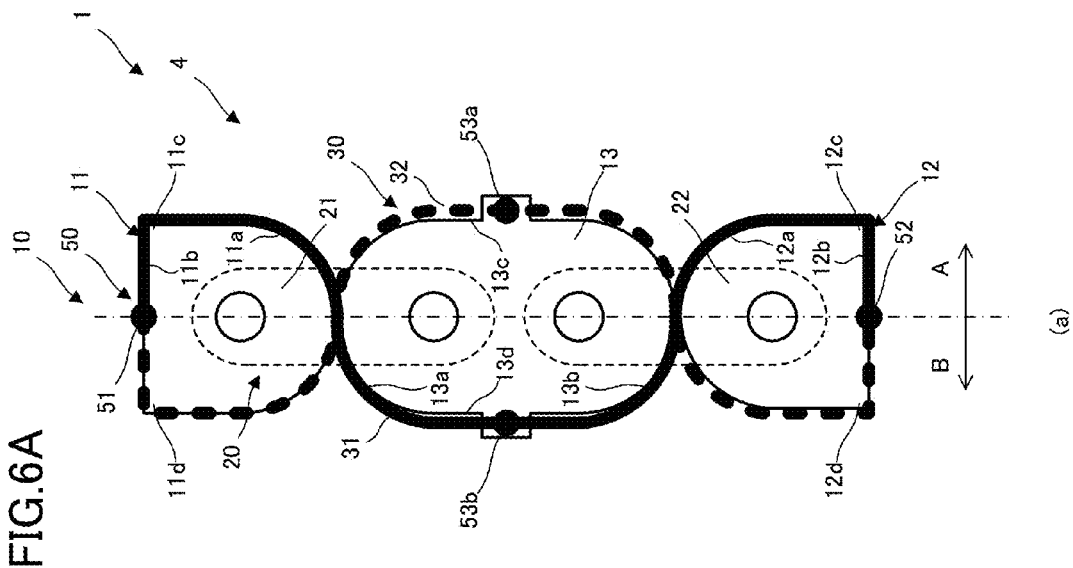

FIGS. 6A and 6B show an example of a portion of the bending assembly 4 in the manipulator 1 according to the second embodiment.

The bending assembly 4 according to the second embodiment may include one to four regulating members 30. Use of two regulating members 30 is here explained.

In the second embodiment, there are two possible fixing modes: a first fixing mode in which both one ends of such first regulating member 31 and second regulating member 32 as shown in FIG. 6A are fixed to the first end surface 11b of the first link member 11 at the first link fixing sites 51 and both the other ends of the first regulating member 31 and second regulating member 32 are fixed to the second end surface 12b of the second link member 12 at the second link fixing sites 52, and a second fixing mode in which both one ends of such first 31 and second regulating member 32 as shown in FIG. 6B are fixed to the intermediate link other-side fixing portion 53b formed on the other-side intermediate surface 13d of the intermediate link member 13 and both the other ends of the first regulating member 31 and the second regulating member 32 are fixed to the intermediate link one-side fixing portion 53a formed on the one-side intermediate surface 13c of the intermediate link member 13.

In the first fixing mode, for instance, the first regulating member 31 is wound from the first link fixing portion 51 on the first end surface 11b of the first link member 11 to the one-side first corner portion 11c, and wound around at least a part on the one side A of the first arc portion 11a. Then, the first regulating member 31 is wound around at least a part on the other side B of the first intermediate arc portion 13a of the intermediate link member 13, and wound around at least a part on the other side B of the second intermediate arc portion 13b via the other-side intermediate surface 13d. Then, the first link member 31 is wound around at least a part on the one side A of the second arc portion 12a of the second link member 12, wound around the one-side second corner portion 12c, and fixed to the second link fixing portion 52 of the second end surface 12b. Further, the first regulating member 31 is fixed to the intermediate link other-side fixing portion 53b formed on the other-side intermediate surface 13d of the intermediate link member 13.

The second regulating member 32 is wound from the first link fixing portion 51 on the first end surface lib of the first link member 11 to the other-side first corner portion 11d, and wound around at least a part on the other side B of the first arc portion 11a. Then, the second regulating member 32 is wound around at least a part on the one side A of the first intermediate arc portion 13a of the intermediate link member 13, and wound around at least a part on the one side A of the second intermediate arc portion 13b via the one-side intermediate surface 13c. Then, the second regulating member 32 is wound around at least a part on the other side B of the second arc portion 12a of the second link member 12, wound around the other-side second corner portion 12d, and fixed to the second link fixing portion 52 of the second end surface 12b. Further, the second regulating member 32 is fixed to the intermediate link one-side fixing portion 53a formed on the surface on one side A of the intermediate link member 13.

In the second fixing mode, it is to be noted that using the intermediate link one-side fixing 53a and intermediate link other-side fixing portion 53b as the fixing positions for one ends and the other ends of the first regulating member 31 and the second regulating member 32, the first regulating member 31 and the second regulating member 32 may be located in such a way as to intersect each other between the first link member 11, the second link member 12 and the intermediate link member 13.

According to the bending assembly 4 in the manipulator 1 according to the second embodiment, it is thus possible to reduce a parts count and, hence, achieve a simplified, easy-to-assemble structure.

FIGS. 7A, 7B and 7C are illustrative of another example of how to wind the regulating member 30 according to the second embodiment.

More specifically, FIG. 7A shows that there is one regulating member 30 provided; FIG. 7B shows that there are three regulating members 30 provided; and FIG. 7C shows that there are four regulating members 3 provided.

In the example of FIG. 7A, the regulating member 30 may be turned or wound and fixed to any of the six fixing sites 50 at one end and the other end. In the example of FIG. 7B, the second regulating member 32 of FIGS. 6A, 6B and 6C is divided into two portions: a portion 32a that connects the first link member 11 to the intermediate link member 13 and a portion 32b that connects the second link member 12 to the intermediate link member 13, providing three regulating members 30. In the example of FIG. 7C, the first regulating member 31 of FIG. 7B is divided into two portions: a portion 31a that connects the first link member 11 to the intermediate link member 13 and a portion 32b that connects the second link member 12 to the intermediate link member 13, providing four regulating members 30.

Figure 8:
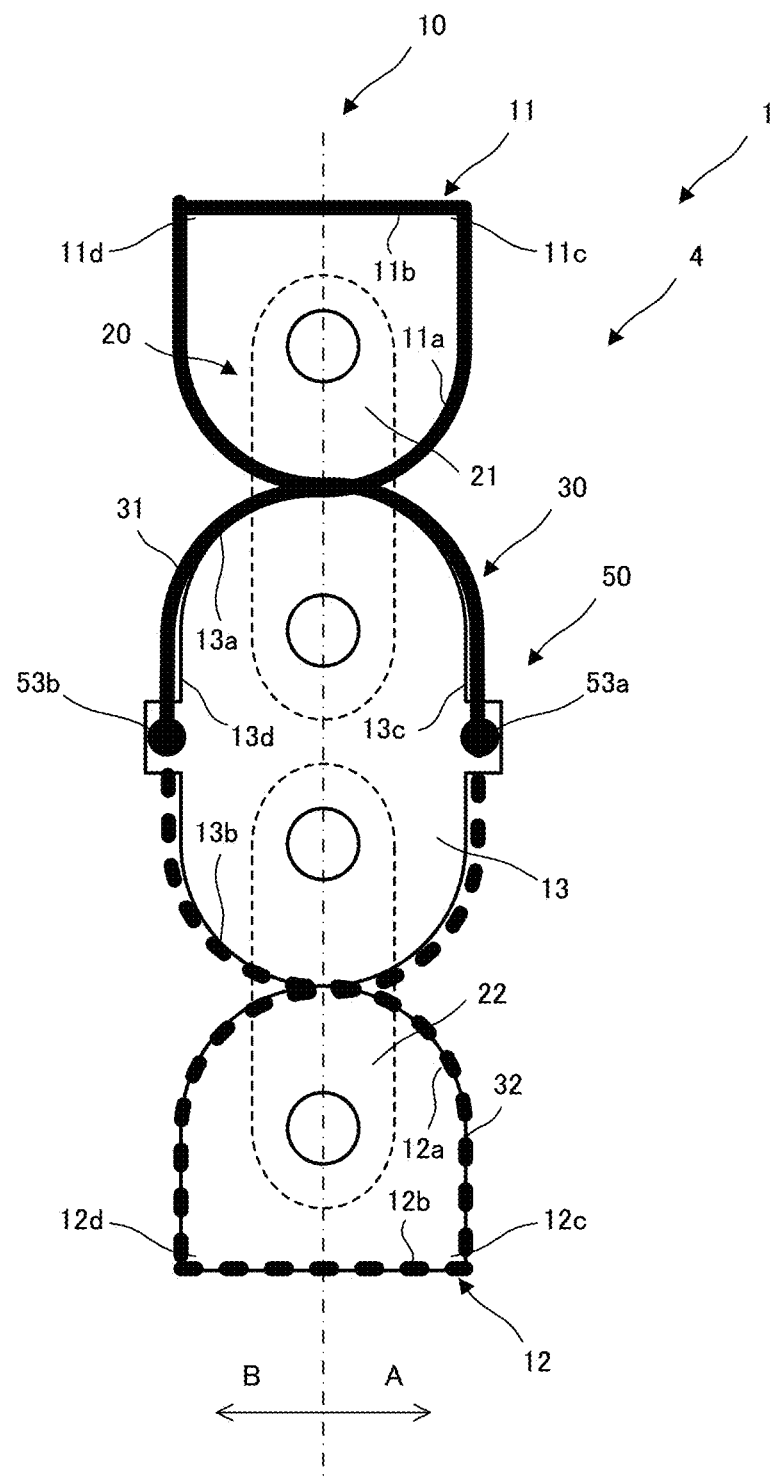
FIG. 8 shows a portion of the bending assembly in the manipulator according to the third embodiment.

FIG. 8 shows a portion of the bending assembly 4 in the manipulator 1 according to the third embodiment.

In the bending assembly 4 according to the third embodiment, one or two regulating members 30 is or are just only fixed to the intermediate one-side fixing portion 53a formed on the one-side intermediate surface 13c of the intermediate link member 13 and the intermediate link other-side fixing portion 53b formed on the other-side intermediate surface 13d. Further, the regulating member 30 is fixed by friction to the first end surface 11b of the first link member 11 and the second end surface 12b of the second link member 12.

When two regulating members 30 are used as an example, the first regulating member 31 is fixed at one end to the intermediate link one-side fixing portion 53a formed on the surface on one side A of the intermediate link member 13. Then, the first regulating member 31 is wound around at least a part on one side A of the first intermediate arc portion 13a of the intermediate link member 13, and wound around at least a part on one side B of the first arc portion 11a of the first link member 11. Then, the first regulating member 31 is wound around the other-side first corner portion 11d, and wound around the one-side first corner portion 11c via the first end surface 11b. Then, the first regulating member 31 is wound around at least a par on the one side A of the first arc portion 11a, wound around at least a part on the other side B of the first intermediate arc portion 13a of the intermediate link member 13, and fixed to the intermediate link other-side fixing portion 53b formed on the surface on the other side B of the intermediate link member 13.

The second regulating member 32 is fixed at one end to the intermediate link one-side fixing portion 53a formed on the surface on one side A of the intermediate link member 13. Then, the second regulating member 32 is wound around at least a part on one side A of the second intermediate arc portion 13b of the intermediate link member 13, and wound around at least a part on the other side B of the first arc portion 12a of the second link member 12. Then, the second regulating member 32 is wound around the other-side second corner portion 12d, and wound around the one-side second corner portion 12c via the second end surface 12b. Further, the second regulating member 32 is wound around at least a part on one side A of the second arc portion 12a, wound around at least a part on the other side B of the second intermediate arc portion 13b of the intermediate link member 13, and fixed to the intermediate link other-side fixing portion 53b formed on the surface on the other side B of the intermediate link member 13.

It is here to be noted that when there is one regulating member 30 used, it may be fixed at one end and the other end to any of the intermediate link one-side fixing portion 53a or the intermediate link other-side fixing portion 53b.

According the bending assembly 4 in the manipulator 1 according to the third embodiment, it is thus possible to fix one or two regulating members 30 at two sites thereby achieving a simplified, easy-to-assemble structure that is capable of smooth actuation.

Figure 9:
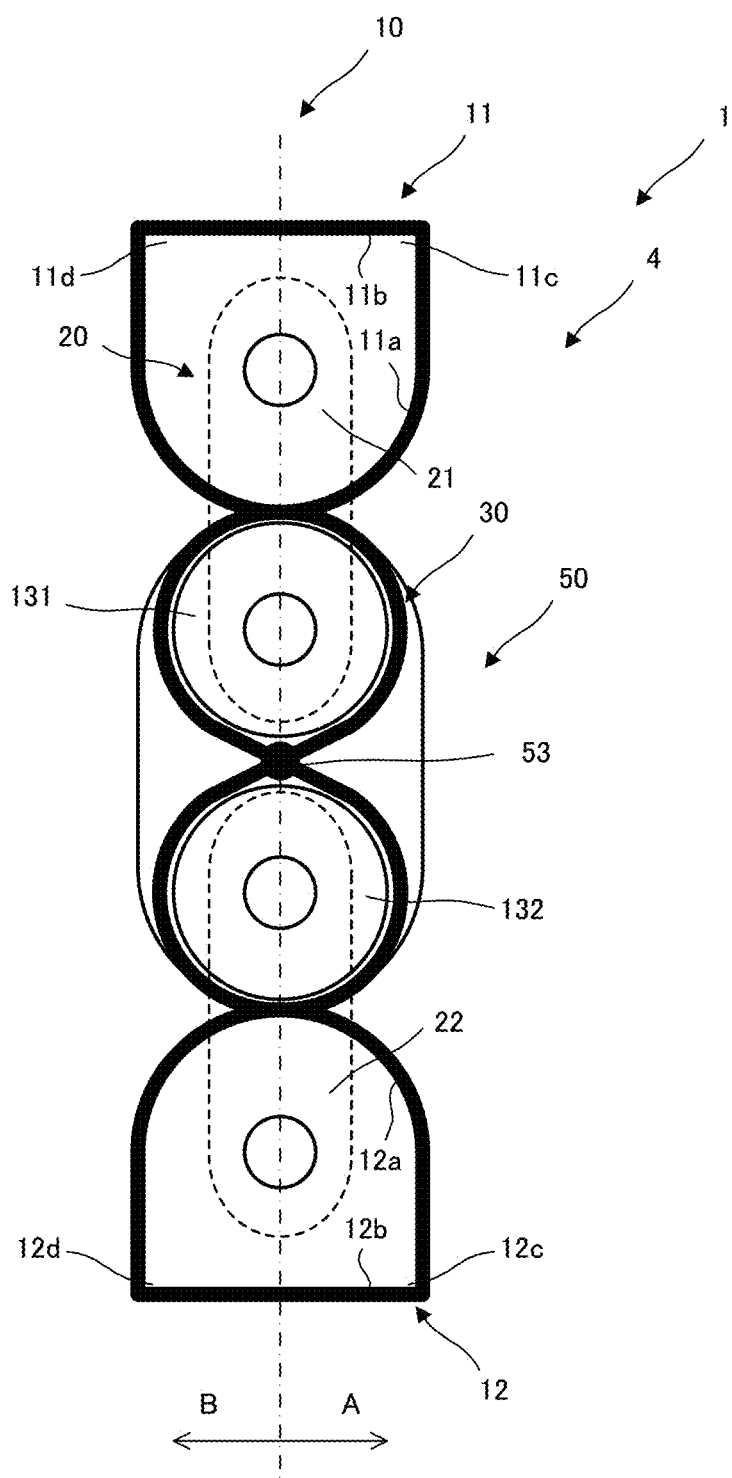
FIG. 9 shows a portion of the bending assembly in the manipulator according to the fourth embodiment.

FIG. 9 shows a portion of the bending assembly 4 in the manipulator 1 according to the fourth embodiment.

In the bending assembly 4 according to the fourth embodiment, the intermediate link member 13 includes a round, rotatable first winding portion 131 and a round, rotatable second winding portion 132. The regulating member 30 is located in such a way as to intersect itself between the first winding portion 131 and the second winding portion 132, and fixed to the point of that intersection. Further, the regulating member 30 is fixed by friction to the first end surface 11b of the first link member 11 and the second end surface 12b of the second link member 12. In the bending assembly 4 according to the fourth embodiment, the single regulating member 30 is thus fixed at a single site.

The bending assembly 4 in the manipulator 1 according to the fourth embodiment can thus be simplified in structure and easy-to-assemble because the single regulating member 30 can be fixed at just one site.

Figure 10:
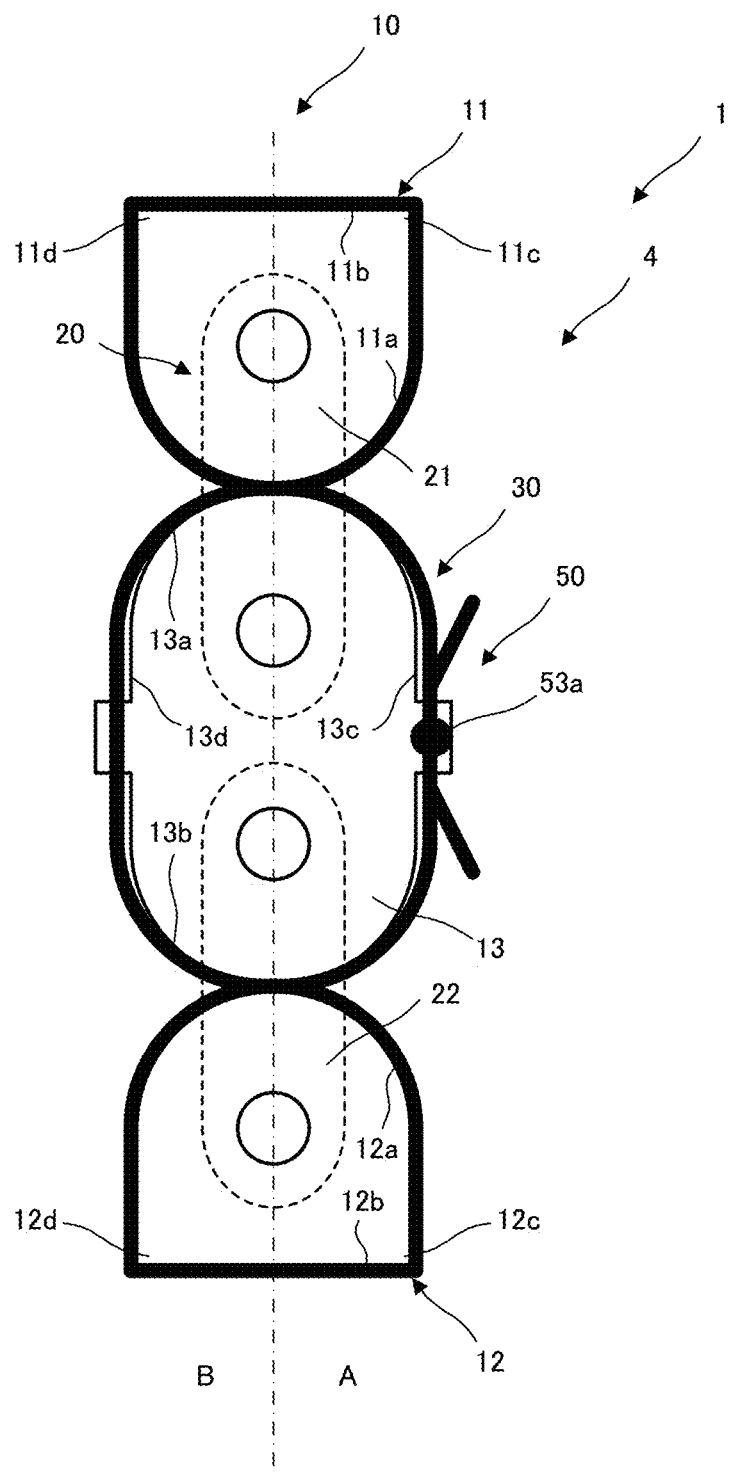
FIG. 10 shows a portion of the bending assembly in the manipulator according to the fifth embodiment.

FIG. 10 shows a portion of the bending assembly 4 in the manipulator 1 according to the fifth embodiment.

In the bending assembly 4 according to the fifth embodiment, the regulating member 30 is just only fixed to the intermediate link one-side fixing portion 53a formed on the one-side intermediate surface 13c of the intermediate link member 13. Further, the regulating member 30 is fixed by friction to the first end surface 11b of the first link member 11 and the second end surface 12b of the second link member 12. In the bending assembly 4 according to the fifth embodiment, the single regulating member 30 is fixed at the single site.

In the bending assembly 4 according to the fifth embodiment, the tension of the regulating member 30 can be applied in one operation to make sure a more simplified, easier-to-assemble structure. Just one site is all that is needed for fixation, making assembling much easier.

Figure 11:
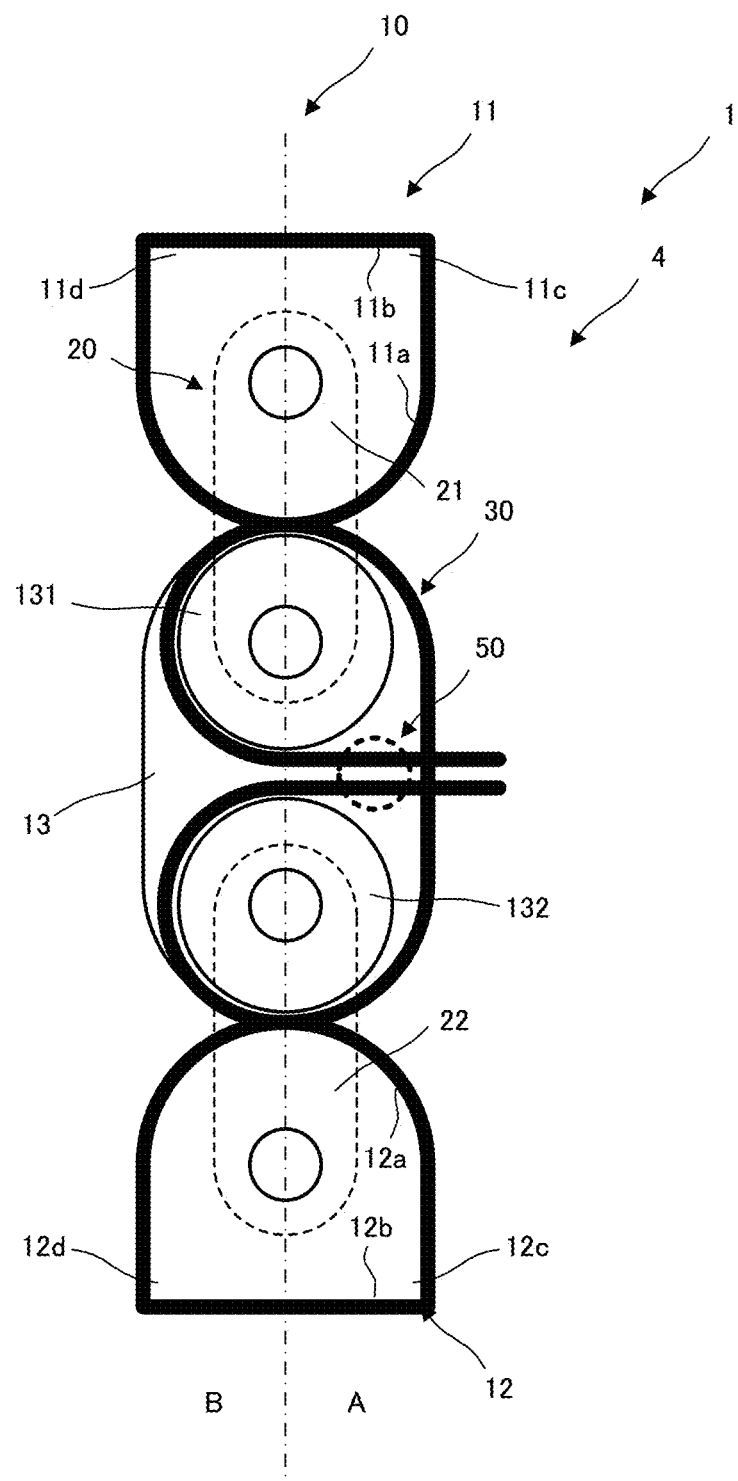
FIG. 11 shows a portion of the bending assembly in the manipulator according to the sixth embodiment.

FIG. 11 shows a portion of the bending assembly 4 in the manipulator 1 according to the sixth embodiment.

In the bending assembly 4 according to the sixth embodiment, the intermediate link member 13 includes a first winding portion 131 and a second winding portion 132, and the single regulating member 30 is wound around those portions such that both its ends are oriented in the same direction from between them. Further, the regulating member 30 is fixed by friction to the first end surface 11b of the first link member 11 and the second end surface 12b of the second link member 12. In the bending assembly 4 according to the sixth embodiment, the single regulating member 30 is fixed at just one site.

In the bending assembly 4 according to the sixth embodiment, it is easy to apply tension on the single regulating member 30 because both its ends are oriented in the same direction.

Figure 12:
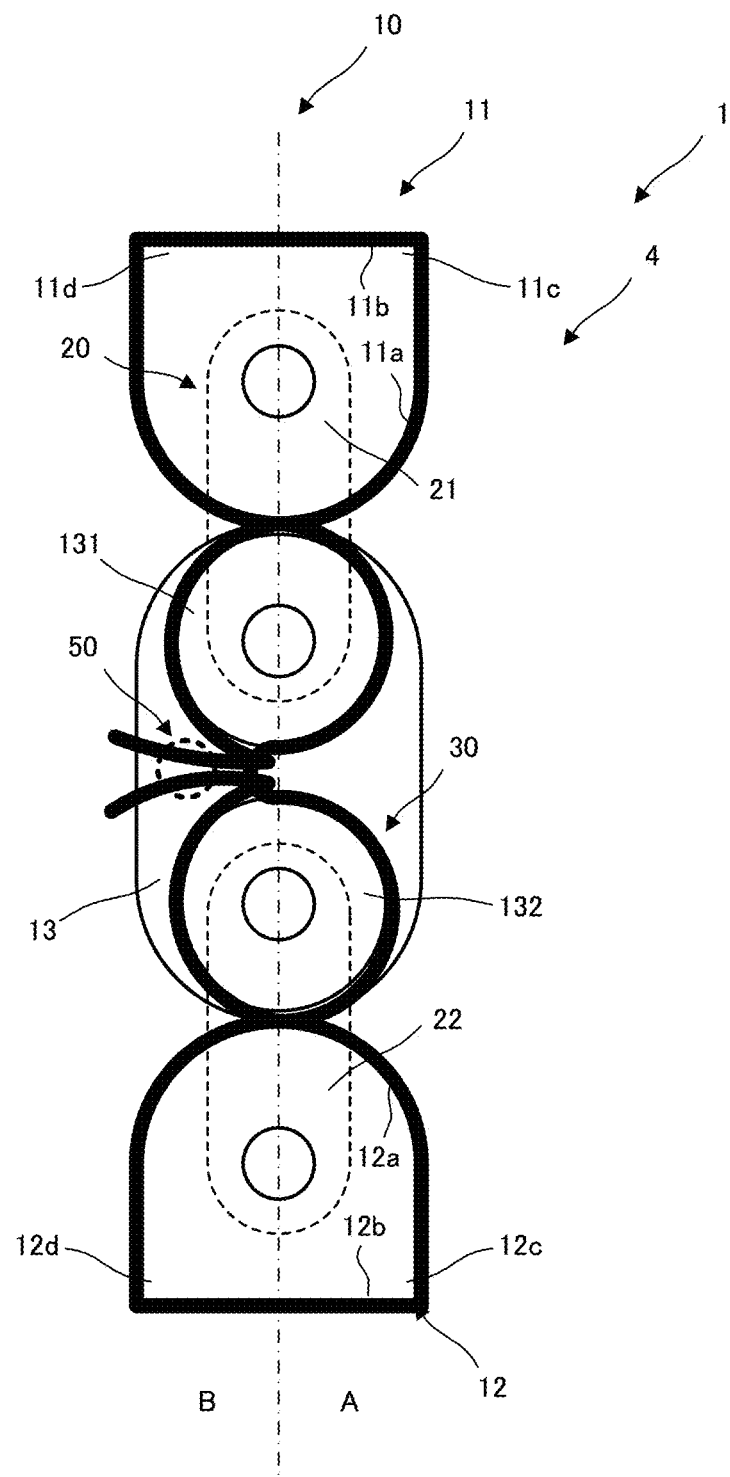
FIG. 12 shows a portion of the bending assembly 4 in the manipulator 1 according to one modification to the sixth embodiment.

FIG. 12 shows a portion of the bending assembly 4 in the manipulator 1 that is a modification to the sixth embodiment.

The bending assembly 4 of FIG. 12 has a structure of catching and pulling the regulating member 30 in a direction toward the other side B, wherein the regulating member 30 lies between the first winding portion 131 and the second winding portion 132 on one side A of the intermediate link member 13 of FIG. 11. Such structure allows both ends of the single regulating member 30 to be oriented in the same direction, making it easy to apply tension on the regulating member 30. Further, the regulating member 30 is unerringly wound around the first winding portion 131 and the second winding portion 132, making it possible to apply uniform tension to them.

Figure 13A:
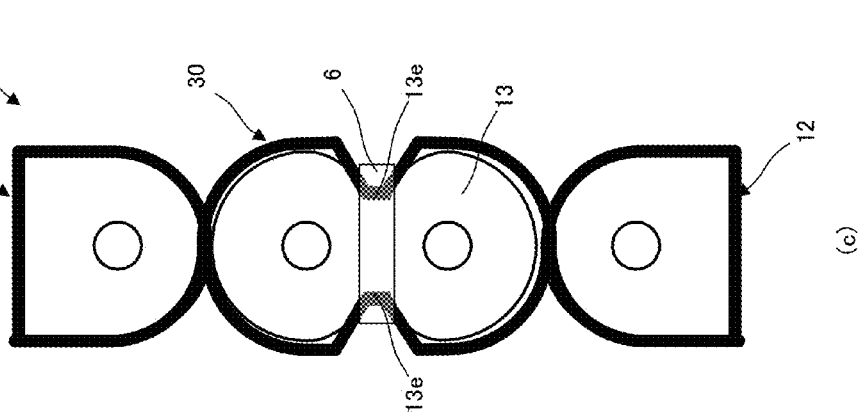
FIGS. 13A, 13B and 13C show one example of the structure of mounting the regulating member in place.
Figure 13B:
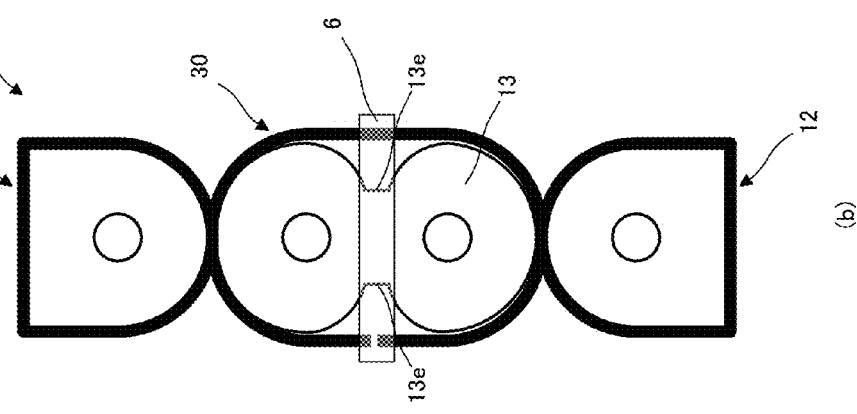
Figure 13C:
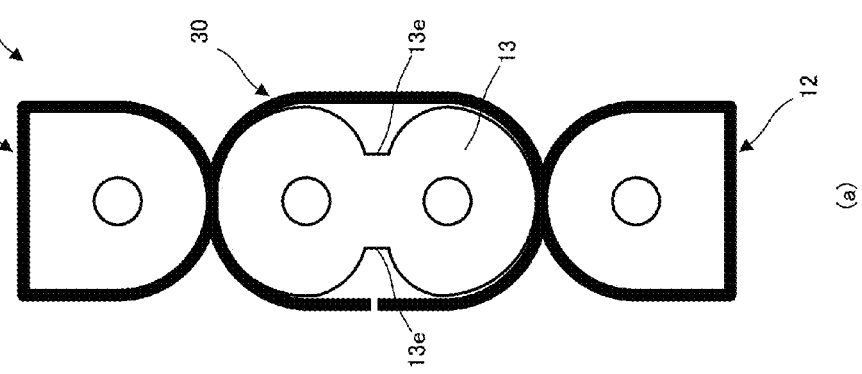

FIGS. 13A, 13B and 13C show one example of the structure of mounting the regulating member 30 in place.

In the example of FIGS. 13A, 13B and 13C, mounting is carried out by caulking. The intermediate link member 13 is recessed at 13e. As shown in FIG. 13A, the regulating member 30 is first wound around the joint portions 10. Then, as shown in FIG. 13B, a caulking member 6 formed of metals, resins or the like is located on the outside of the regulating member 30 in conformity with the position of the recess 13e. Then, as shown in FIG. 13C, the caulking member 6 is caulked.

Such caulking structure makes it easy to fix the regulating member 30 in place while, at the same time, putting the tension of the regulating member 30 in action.

Figure 14:
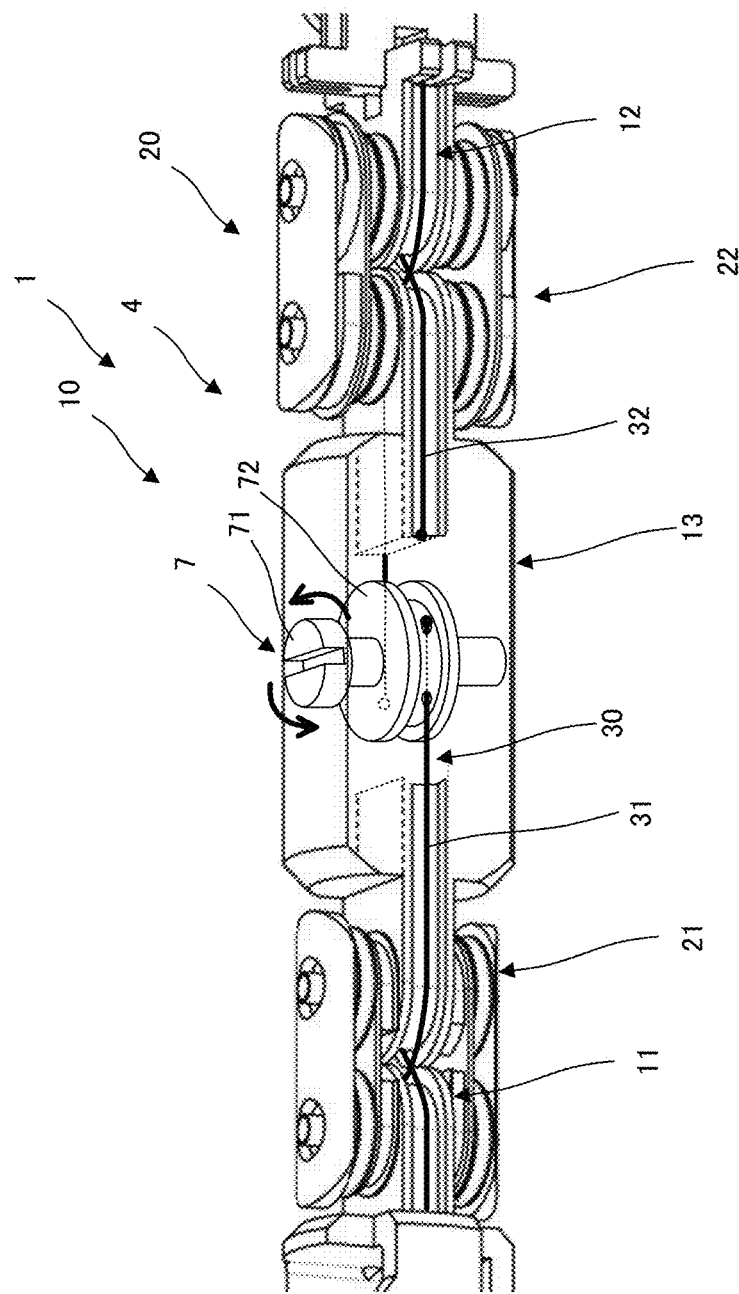
FIG. 14 shows one example of a structure of adjusting the tension of the regulating member.

FIG. 14 shows one example of the structure of adjusting the tension of the regulating member 30.

In the example of FIG. 14, the intermediate link member 13 is provided with a tension adjustor member 7. The tension adjustor member 7 includes a threaded portion 71 capable of being rotated as by a screwdriver, and a rotary portion 72 to which one end of the regulating member 30 is attached and which is rotatable together with the threaded portion 71. In the example of FIG. 14, the regulating member 30 includes a first regulating member 31 and a second regulating member 32. One ends of the first 31 and the second regulating member 32 are mounted in a symmetrical position with respect to the center of rotation of the rotary portion 72. As is the case with the third embodiment of FIG. 8, the first regulating member 31 is wound around the first link member 11, and then fixed at the other end to the intermediate link member 13. As is the case with the third embodiment of FIG. 8, the second regulating member 32 is wound around the second link member 12, and then fixed at the other end to the intermediate link member 13.

Upon adjustment of the tension of the regulating member 30, the threaded portion 71 of the tension adjustment member 7 is turned as by a screwdriver, whereupon the rotary portion 72, to which one end of the regulating member 30 is attached, rotates to pull the regulating member 30. Such structure makes sure easy tension adjustment.

Figure 15:
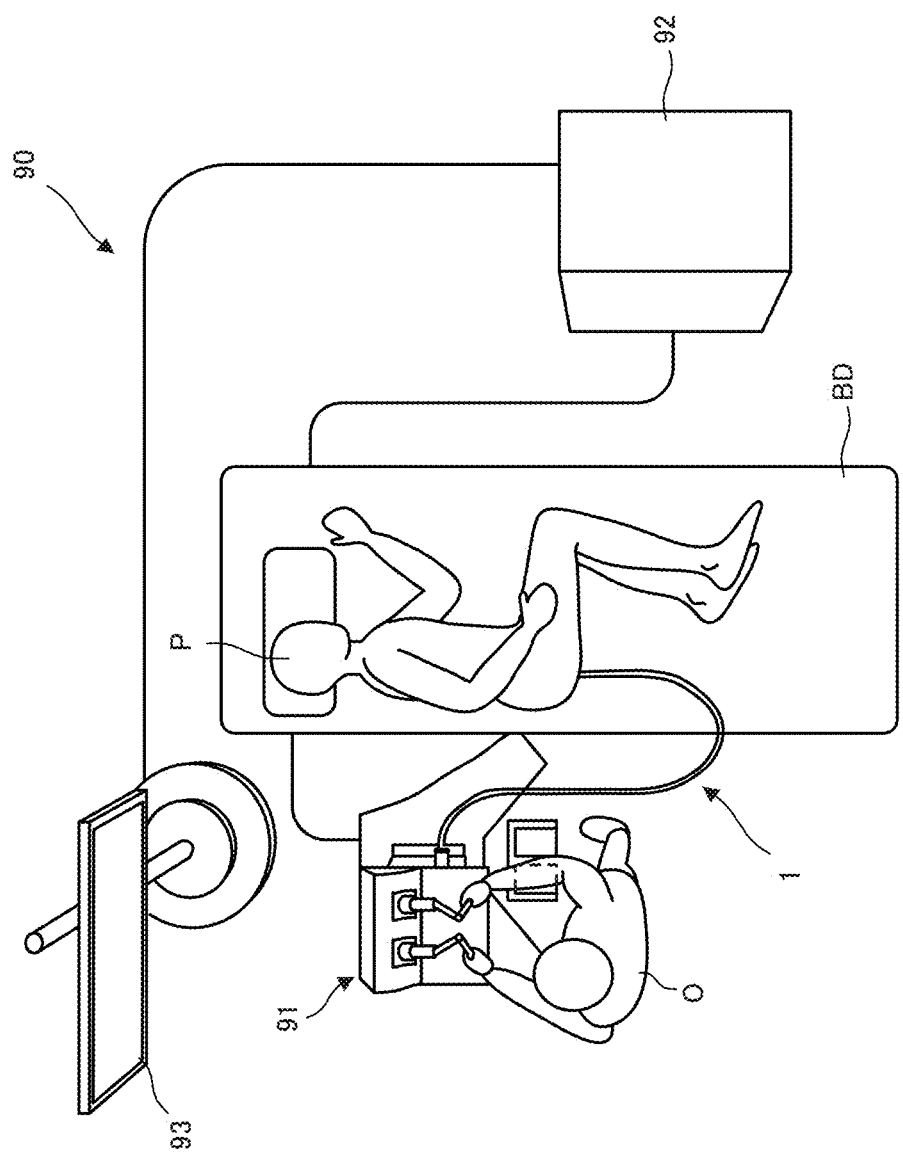
FIG. 15 shows the manipulator system to which the manipulator described herein is applied.
Figure 16:
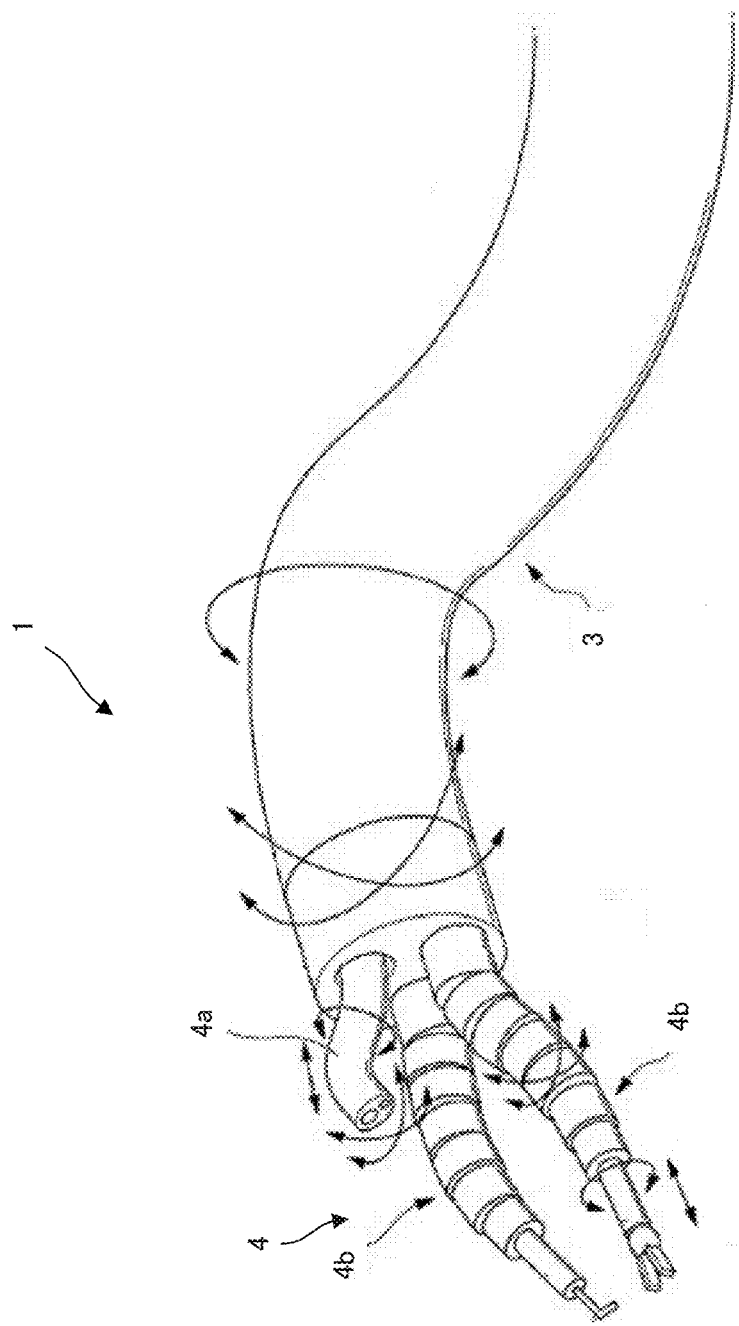
FIG. 16 shows one example of the distal end of the manipulator described herein.
Figure 17:
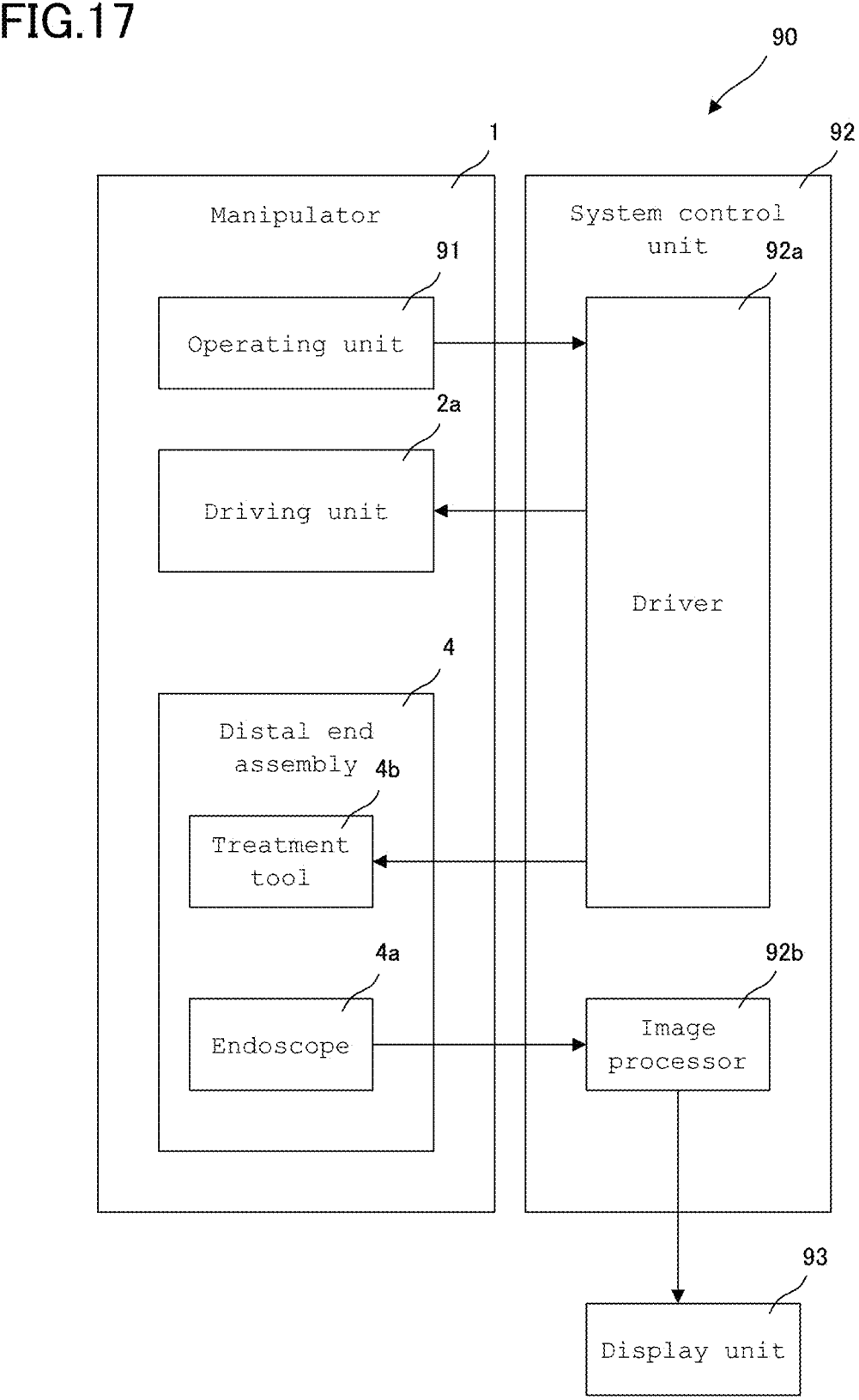
FIG. 17 is illustrative in architecture of the manipulator system to which the manipulator described herein is applied.

FIG. 15 shows a manipulator system 90 to which the manipulator 1 described herein is applied. FIG. 16 is illustrative of an example of the bending assembly 4 in the manipulator 1 described herein, and FIG. 17 is illustrative in architecture of the manipulator system 90 to which the manipulator 1 described herein is applied.

Applied to the manipulator system 90 described herein is the manipulator 1 of FIG. 1. The manipulator system 90 includes an operating unit 91 that is put by an operator O into operation, an elongated component 3 of FIG. 1 that can be inserted into the body of a patient P lying on an operating table BD, for instance, a soft organ such as the large intestine, a manipulator 1 including an endoscope or the like provided on the distal end of the elongated component 3, a bending assembly 4 shown in FIG. 1, etc., a control unit 92 that controls the manipulator 1 and a display unit 93 that displays images acquired through the manipulator 1.

As depicted in FIG. 15, the operating unit 91 includes a pair of handles attached to an operating base, a footswitch and so on located on the floor surface. The operating unit 91 may have a multi-joint structure. The operating unit 91 is mechanically connected to the elongated component 3 and bending assembly 4 for bending operation of the elongated component 3. In response to signals about the angle of the operating unit 91 in operation, acquired by an angle acquisition portion such as an encoder, the control unit 92 puts the bending assembly 4 into actuation via a driver 92*a*.

In the manipulator 1, as depicted in FIG. 16, the bending assembly 4 may be an endoscope 4*a* and a treatment tool 4*b* having a flexing or bending assembly or, alternatively, it may be a guide tube having a bending assembly, through which a conventional joint-free treatment tool is inserted. The endoscope 4*a* includes a viewing optical system and a lighting optical system that light up the interior of the body and gain images, an imaging device, and such. An image gained by the imaging device through the viewing optical system is sent out to an image processor 92*b* in the control unit 92, and an image processed in the image processor 92*b* is displayed on the display unit 93. In this state, the operator O operates the manipulator 1 while viewing images displayed on the display unit 93.

Such manipulator system 90 can be put into stable and smooth actuation.

As described above, the manipulator 1 described herein includes an operating unit 2*b*, and a bending assembly 4 that is bent by operation of the operating unit 2*b*, wherein the bending assembly 4 includes a first link member 11 having a first arc portion 11*a*, a second link member 12 having a second arc portion 12*a*, an intermediate link member 13 mounted between the first link member 11 and the second link member 12, a first coupling member 21 that couples the first link member 11 to the intermediate link member 13, a second coupling member 22 that couples the second link member 12 to the intermediate link member 13, and a regulating member 30 that intersects itself between, and is wound around, the first arc portion 11*a* of the first link member 11 and the first intermediate arc portion 13*b* of the intermediate link member 13 and intersects itself between, and is wound around, the second arc portion 12*a* of the second link member 12 and the second intermediate arc portion 13*b* of the intermediate link member 13 such that the first arc portion 11*a* and the first intermediate arc portion 13*a* as well as the second arc portion 12*a* and the second intermediate arc portion 13*b* roll. Thus, the manipulator 1 has a reduced parts count and a simplified, easy-to-assemble structure, and is put into smooth actuation.

In the manipulator 1 described herein, the regulating member 30 is a linear member 30 that intersects itself between the first arc portion 11*a* of the first link member 11 and the first intermediate arc portion 13*a* of the intermediate link member 13 and intersects itself between the second arc portion 12*a* of the second link member 12 and the second intermediate arc portion 13*b* of the intermediate link member 13. Thus, the manipulator 1 has a more simplified, easy-to-assemble structure, and is put into smooth actuation.

In the manipulator 1 described herein, the linear member 30 is fixed to the intermediate link member 13. It is thus possible to apply tension unerringly and, hence, put the manipulator 1 into stable actuation.

In the manipulator 1 described herein, the linear member 30 is fixed to the first link member 11. It is thus possible to apply tension unerringly and, hence, put the manipulator 1 into stable actuation.

In the manipulator 1 described herein, the linear member 30 is fixed to the second link member 13. It is thus possible to apply tension unerringly and, hence, put the manipulator 1 into stable actuation.

In the manipulator 1 described herein, both ends of the linear member 30 are fixed to the intermediate link member 13; a single linear member 30 is all that is needed. Thus, the manipulator 1 has a more simplified, easy-to-assemble structure for smooth actuation.

In the manipulator 1 described herein, the linear member 30 includes a first linear member 31 and a second linear member 32, wherein the first linear member 31 is fixed at one end to the first link member 11, wound from the first arc portion 11*a* to the first intermediate arc portion 13*a* of the intermediate link member 13, wound from the first intermediate arc portion 13*a* to the second intermediate arc portion 13*b*, wound from the second intermediate arc portion 13*b* to the second arc portion 12*a* of the second link member 12, and fixed at the other end to the second link member 12; the second linear member 32 is fixed at one end to the first link member 11, wound from the first arc portion 11*a* to the first intermediate arc portion 13*a* of the intermediate link member 13, wound from the first intermediate arc portion 13*a* to the second intermediate arc portion 13*b*, wound from the second intermediate arc portion 13*b* to the second arc portion 12*a* of the second link member 12, and fixed at the other end to the second link member 12; and the first linear member 31 and the second linear member 32 intersect each other between the first arc portion 11*a* of the first link member 11 and the first intermediate arc portion 13*a* of the intermediate link member 13 and intersect each other between the second arc portion 12*a* of the second link member 12 and the second intermediate arc portion 13*b* of the intermediate link member 13. Unerring application of tension on the manipulator 1 makes sure stable actuation of the manipulator 1.

In the manipulator 1 described herein, the linear member 30 is located in a groove formed in the intermediate link member 13. Thus, the wire 30 is never out of the intermediate link member 13, making sure stable actuation.

In the manipulator 1 described herein, the intermediate link member 13 includes a tension adjustor 7 that adjusts a tension of the linear member 30. More unerring application of tension makes sure stable actuation.

The manipulator system 90 described herein includes the aforesaid manipulator 1 with a treatment tool 4b and an endoscope 4a included in the bending assembly 4, an image processor 92a for applying image processing to an image signal obtained from the endoscope 4a, and a display unit 93 for displaying an image signal sent from the image processor 92a. This makes sure smooth actuation.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

For instance, the joint component 10 may be built up not only of coaxial joints but also of a combination of joints having axes reversed at 90°.

REFERENCE SIGNS LIST

1: Manipulator
2: Main unit
3: Elongated component
4: Bending assembly
5: Power transmission component
10: Joint component
11: First link member
12: Second link member
13: Intermediate link member
20: Coupling member
21: First coupling member
22: Second coupling member
30: Linear member (regulating member)
31: First regulating member
32: Second regulating member
50: Fixing sites
90: Manipulator system
91: Operating unit
92: System control unit
93: Display unit

The invention claimed is:
1. A manipulator comprising:
an operating unit, and
a bending assembly that is bent by operation of the operating unit,
wherein:
the bending assembly includes:
a first link member having a first arc portion,
a second link member having a second arc portion,
an intermediate link member that includes a first intermediate arc portion and a second intermediate arc portion in opposition to the first intermediate arc portion, and is mounted between the first link member and the second link member,
a first coupling member having a plurality of centers of rotation for coupling the first link member to the intermediate link member rotatably,
a second coupling member having a plurality of centers of rotation for coupling the second link member to the intermediate link member rotatably, and
a linear member comprised of two portions, the two portions being a first regulating member and a second regulating member,
the first regulating member is fixed at one end to the first link member and is fixed at a second end to the second link member, wherein there is a line bisected by, and that connects, the centers of rotation of the first coupling member and the centers of rotation of the second coupling member, and the first regulating member is wound around from a first side of the line to a second side of the line, the second side opposite the first side, through a space between the first arc portion of the first link member and the first intermediate arc portion of the intermediate link member and again around the second side of the line from the first side through a space between the second arc portion of the second link member with the second intermediate arc portion of the intermediate link member, to regulate the first link member and the second link member such that the first arc portion and the first intermediate arc portion as well as the second arc portion and the second intermediate arc portion roll, and
the second regulating member, that, on the line bisected by, and connecting, the centers of rotation of the first coupling member and the second coupling member is wound so as to be positioned on a side opposite to the first regulating member on each link member and fixed to the first link member and fixed to the second link member,
wherein the intermediate link member includes a tension adjustor that adjusts a tension of the linear member.
2. The manipulator according to claim 1,
wherein the first regulating member is fixed at its middle part to the intermediate link member, and wherein the second regulating member is fixed at its middle part to the intermediate link member.
3. The manipulator according to claim 1,
wherein the linear member is located in a groove formed in the intermediate link member.

* * * * *